(12) United States Patent
Carriazo

(10) Patent No.: US 7,037,337 B2
(45) Date of Patent: May 2, 2006

(54) IMPLANT FOR ALTERING THE IRIS COLOR AND METHOD OF LOCATING AND FIXING AN IMPLANT FOR ALTERING THE IRIS COLOR

(76) Inventor: Cesar C. Carriazo, Calle 86 No. 49C-69, Baranquilla (CO)

( * ) Notice: Subject to any disclaimer, the term of this patent is extended or adjusted under 35 U.S.C. 154(b) by 0 days.

(21) Appl. No.: 10/666,727

(22) Filed: Sep. 19, 2003

(65) Prior Publication Data

US 2004/0102844 A1  May 27, 2004

(51) Int. Cl.
  *A61F 2/14* (2006.01)
(52) U.S. Cl. ...................................... 623/4.1
(58) Field of Classification Search ......... 623/4.1–6.18
  See application file for complete search history.

(56) References Cited

U.S. PATENT DOCUMENTS

| | | | | |
|---|---|---|---|---|
| 2,497,873 A | * | 2/1950 | Erpf | 623/6.64 |
| 3,991,426 A | * | 11/1976 | Flom et al. | 623/6.12 |
| 4,366,582 A | * | 1/1983 | Faulkner | 623/6.55 |
| 4,446,581 A | * | 5/1984 | Blake | 623/6.43 |
| 4,592,752 A | * | 6/1986 | Neefe | 424/429 |
| 5,034,166 A | * | 7/1991 | Rawlings et al. | 264/1.7 |
| 5,628,797 A | * | 5/1997 | Richer | 623/6.2 |
| 6,149,685 A | * | 11/2000 | Sigoloff | 623/4.1 |
| 6,221,106 B1 | | 4/2001 | Hermeking | |
| 6,280,469 B1 | * | 8/2001 | Terry et al. | 623/4.1 |
| 6,543,453 B1 | * | 4/2003 | Klima et al. | 128/898 |
| 2004/0006387 A1 | * | 1/2004 | Kelman | 623/6.36 |
| 2004/0143324 A1 | * | 7/2004 | Melles | 623/4.1 |
| 2004/0153148 A1 | * | 8/2004 | Kahn | 623/4.1 |
| 2005/0213028 A1 | * | 9/2005 | Strebig | 351/162 |

FOREIGN PATENT DOCUMENTS

| | | |
|---|---|---|
| DE | 3926536 | 2/1991 |
| DE | 19850807 | 5/2000 |
| FR | 2696340 | 4/1994 |
| FR | 2696340 | * 8/1994 |
| FR | 2728459 | 6/1996 |
| WO | WO 99/62434 | 12/1999 |
| WO | WO 01/66040 | 9/2001 |
| WO | WO 01/87188 | 11/2001 |

\* cited by examiner

*Primary Examiner*—Suzette J-J Gherbi
(74) *Attorney, Agent, or Firm*—Womble, Carlyle, Sandridge & Rice, PLLC

(57) ABSTRACT

The present invention discloses an implant for altering the iris color, consisting of a completely or partially transparent, semi-transparent or non-transparent, colored, biocompatible and flexible material, wherein the implant is formed annularly, and forms an annular area coming to rest on the iris of an eye, and comprises a central circular opening, wherein at least one attaching means is formed for detachable attachment of the implant the iris. The attaching means is disposed within the annular area of the implant. The invention further discloses methods of locating and fixing an implant for altering the iris color.

17 Claims, 5 Drawing Sheets

IMPLANT FOR ALTERING THE IRIS COLOR AND METHOD OF LOCATING AND FIXING AN IMPLANT FOR ALTERING THE IRIS COLOR

CROSS-REFERENCE TO RELATED APPLICATIONS

This application claims priority on European patent application number 02 021 188.4, filed on Sep. 24, 2002.

INCORPORATION BY REFERENCE

The specification of European patent application number 02 021 188.4 is incorporated herein in its entirety, by this reference.

BACKGROUND OF THE INVENTION

The present invention relates to an implant for altering the iris color, consisting of a completely or partially transparent, semi-transparent or non-transparent, colored, biocompatible and flexible material, wherein the implant is formed annularly and forms an annular area coming to rest on the iris of an eye, and comprises a central circular opening. For detachable attachment of the implant to the iris, at least one attaching means is formed.

The present invention further relates to methods of locating and fixing an implant for altering the iris color.

Such an implant for altering the iris color is known from the DE 198 50 807 A1. It describes an artificial iris system having a color formation and structure, which is identical to the given eye or individual, respectively, and having functions for simulation of the natural eye functions, especially the light-dependent stopping down effect of the pupil. Furthermore, DE 198 50 807 describes a method of manufacturing the artificial iris system, wherein by combining preferably transparent or semi-transparent colored foils and by abrading undesired colored foil portions a desired color mixture is obtained. For simulation of the natural eye functions, especially the pupil function, the artificial iris is provided with means for attenuating the light transmission through an open area corresponding to the pupil. The known artificial iris can be realized as a contact lens or as an implant. In the latter case, the implant has a peripheral anchoring apparatus as an attaching member in order to allow for different fixation locations in different eyes. Therein, the implant can be disposed in the capsule sac, in the sulcus or in the anterior chamber of the eye.

Further, the U.S. Pat. No. 5,628,797 (Richer) describes an intraocular lens implant, which is disposed in the anterior eye chamber. Therein, the implant consists of a transparent material, especially of transparent plastics such as polymethacrylate (PMMA). Additionally, it consists of two ring halves, which can be combined to a closed ring, wherein the annular area comes to rest on the pupil of the eye. For attaching the implant, attaching means are in turn disposed peripherally at the implant, which engage with corresponding regions of the eye.

However, the known implants for altering the iris color are disadvantageous in that they each have attaching means gripping and protruding peripherally beyond the actual implant, respectively, and thus can result in intraocular injuries in this region. This is especially true in the surgical insertion of the implants into the eye.

SUMMARY OF THE INVENTION

Therefore, it is an object of the present invention to provide an implant of the type mentioned at the beginning and methods of locating and fixing an implant for altering the iris color, which ensure a simple and gentle attachment of the implant within the eye.

In an implant according to the invention for altering the iris color, one or more attaching means are disposed within the annular area formed by the annular implant. Advantageously, thereby it is ensured that no peripheral protrusions or other attaching means protrude from the circumference of the implant outwardly into the surroundings, i.e. into regions within an eye. Thus, on the one hand, already in surgical insertion of the implant according to the invention into the eye, it is avoided that traumas within the surgical region in or at the eye arise. On the other hand, also possible injuries after the intraocular placement of the implant on the iris are nearly excluded. The implant according to the invention is ideally suitable as an implant for altering the iris color, since it consists of a completely or partially transparent, semi-transparent or non-transparent, colored, biocompatible and flexible material. Also the introduction of the implant into the eye is practicable simply and quickly by way of the flexible design of the implant.

In an advantageous development of the implant according to the invention, the attaching means consists of at least one opening in the annular area, wherein the opening serves for passing and anchoring the underlying partial areas of the iris. Therein, passing and anchoring the corresponding iris areas can be effected in simple manner by a suction or vacuum device, respectively. However, it is also possible to manually pass the iris areas through the opening or the openings in the implant, respectively, and to anchor them. In an advantageous development of the invention, the opening is formed in the shape of cross-slits. Such a formation ensures the secure retention of the iris areas passed through the opening or openings, respectively, on the implant.

In a further advantageous development of the implant according to the invention, the attaching means consists of at least one hook-like protrusion, the protrusion serving for penetrating and hooking the implant into the corresponding partial areas of the iris. Such a protrusion or such protrusions, respectively, allow(s) for quick and simple attachment of the implant onto the iris. For easier penetration of the protrusions into the corresponding iris areas, the protrusion or the protrusions each can include an exposed end, which is formed tapered. Advantageously, the protrusion additionally consists of biocompatible material. This is also true for the entire implant. Especially, the implant and/or the protrusion consist of biocompatible plastics.

In another advantageous development of the implant according to the invention, an optical lens or a transparent foil is disposed in the central opening of the implant. Thereby it is possible, besides the alteration or reinforcement of the iris, to also effect corrections of the visual acuity of the eye.

In another advantageous development of the invention, the implant is printable, thereby it is possible to apply every conceivable design, i.e. every conceivable color or every pattern, without problem onto the implant. Additionally, it is possible that the edges of the implant are formed completely or partially irregularly or serrated. Thereby, individual and unique visual alterations not only of the iris color, but also of the shape of the iris itself result.

In an advantageous development of the invention, the implant has a diameter of 5 to 12 mm and a thickness of 50 to 300 μm. The central circular opening has a diameter adapted to the diameter of the implant of 5 to 7 mm. By such sizing of the implant, it is possible to adapt it to nearly every eye or iris size, respectively. The thickness of only 50 to 300 μm supports the advantageous flexible formation of the implant.

In accordance with the objectives of the invention there are provided several methods of locating and fixing an implant for altering the iris color. In general a method of locating and fixing an intraocular implant for altering the iris color is provided comprising the steps of:

a) preparing an eye to receive an intraocular implant;
b) inserting the intraocular implant into the eye via a small cut in the eye;
c) positioning said implant on the iris of the eye, wherein said implant consists of a completely or partially transparent, semi-transparent or non-transparent, colored, biocompatible and flexible material and wherein said implant is formed annularly, and forms an annular area coming to rest on the iris of said eye, said implant further comprising a central circular opening and at least one attaching means for a detachable attachment of the implant to the iris, wherein said attaching means is disposed within the annular area;
d) attaching said implant to the iris; and
e) closing the eye where said implant was inserted.

BRIEF DESCRIPTION OF THE DRAWINGS

Other objects, advantages, and features of the present invention will become more fully apparent from the following detailed description of the preferred embodiment, the appended claims and the accompanying drawings in which:

DESCRIPTION OF THE PREFERRED EMBODIMENTS

Figure 1:
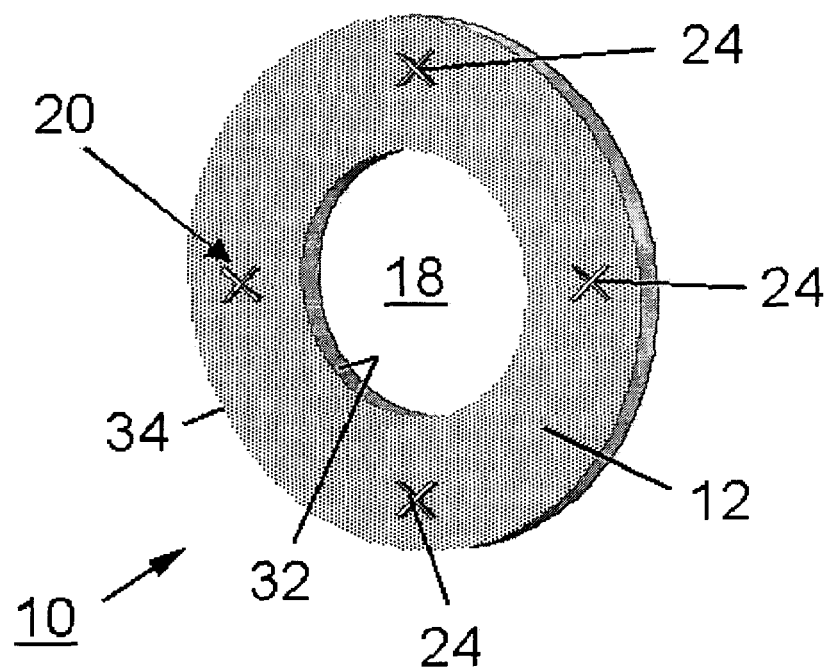
FIG. 1 is a schematic representation of an inventive implant according to a first embodiment.

FIG. 1 shows in a schematic representation an implant 10 for altering the iris color according to a first embodiment. One recognizes that the implant 10 is formed annularly and has an annular area 12, which comes to rest on the iris 16 of an eye 14 (cf. FIG. 2). Additionally, a central circular opening 18 is formed in the implant, which comes to rest in the region of a pupil 38 of the eye 14 (cf. FIG. 2) after disposing the implant 10 on the iris 16.

Further, one recognizes in the illustrated first embodiment of the implant 10, that within the annular area 12 several attaching means 20 are disposed. Therein, the attaching means 20 each consist of an opening 24 extending through the annular area 12. Therein, the openings 24 serve for passing and anchoring the underlying partial areas of the iris 16. In the illustrated embodiment, the openings 24 are formed in the shape of cross-slits. However, every other shape of the openings 24 is also conceivable. Further, the openings 24 can have protrusions and/or a rough surface at their inner circumference. Thereby, a strong anchorage of the corresponding iris areas in the openings 24 is ensured.

Further, one recognizes that the annular implant 10 has corresponding edges 32 and 34. In the illustrated first embodiment, the edges 32, 34 are formed uniformly circularly.

The implant 10 usually consists of a completely or partially transparent, semi-transparent or non-transparent flexible material. Additionally, the material is formed colored and biocompatible. Especially, the implant consists of biocompatible plastics. Herein, it can be the plastics PMMA. In addition, the implant is printable.

Therein, the implant 10 has a diameter of 5 to 12 mm and a thickness of 50 to 300 μm. The central circular opening 18 has a diameter adapted to the diameter of the implant 10 of 5 to 7 mm. Therein, the implant 10 can be manufactured from one piece or also from a plurality of single elements such as a plurality of superimposed foils.

Figure 2:
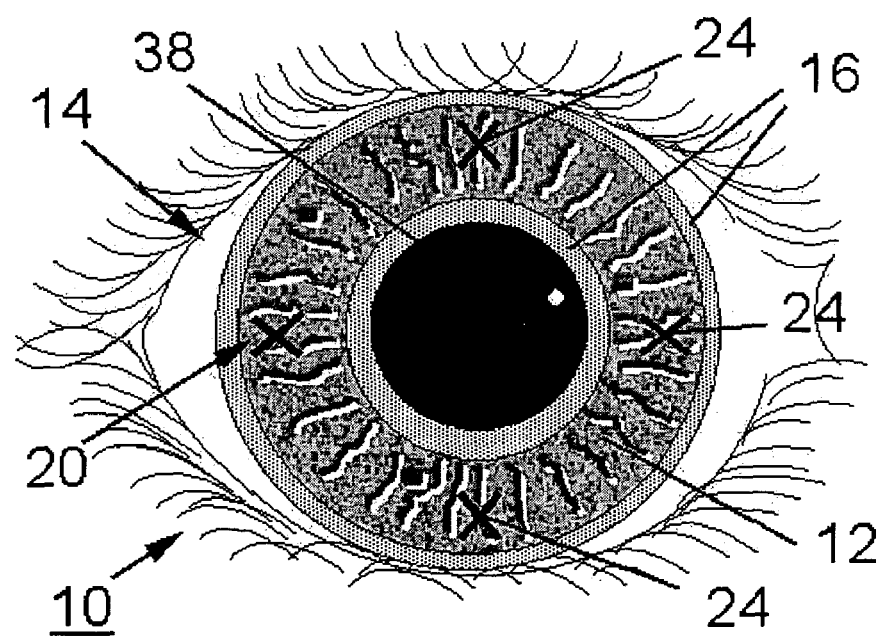
FIG. 2 is a representation of the implant according to FIG. 1, wherein the implant rests on an iris.

FIG. 2 shows a representation of the implant 10 according to FIG. 1, wherein the implant 10 rests in the iris 16. One recognizes that the attaching means 20, 24 in the shape of cross-slits are formed in the annular area 12 of the implant 10, and thus rest on corresponding partial areas of the iris 16. The central opening 18 of the implant 10 allows for the transmission of light through the pupil 38 into the eye 14.

Figure 3:
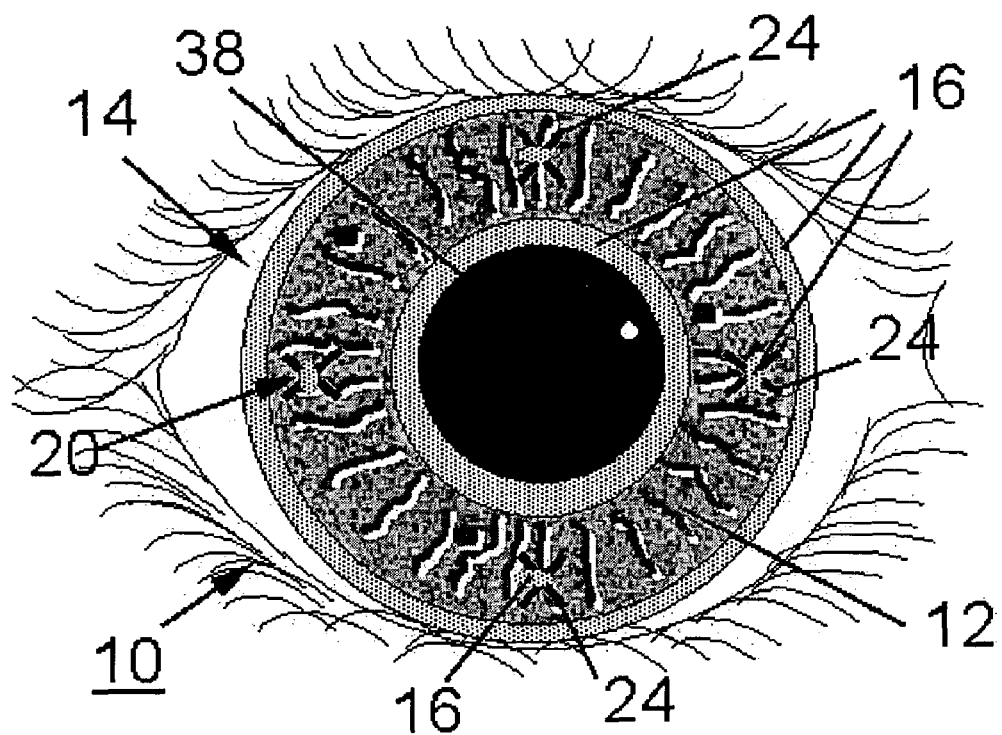
FIG. 3 is a representation of the implant according to FIGS. 1 and 2, wherein the implant rests on an iris and is attached thereto.

FIG. 3 shows a representation of the implant 10 according to FIGS. 1 and 2, wherein the implant 10 rests on the iris 16 and is attached thereto. From this figure, it is seen that the partial areas of the iris 16 underlying the openings 24 are passed through the openings 24 and are attached and anchored in or by these, respectively. Therein, the formation of the openings 24 in the shape of cross-slits supports the retaining effect.

Figure 4:
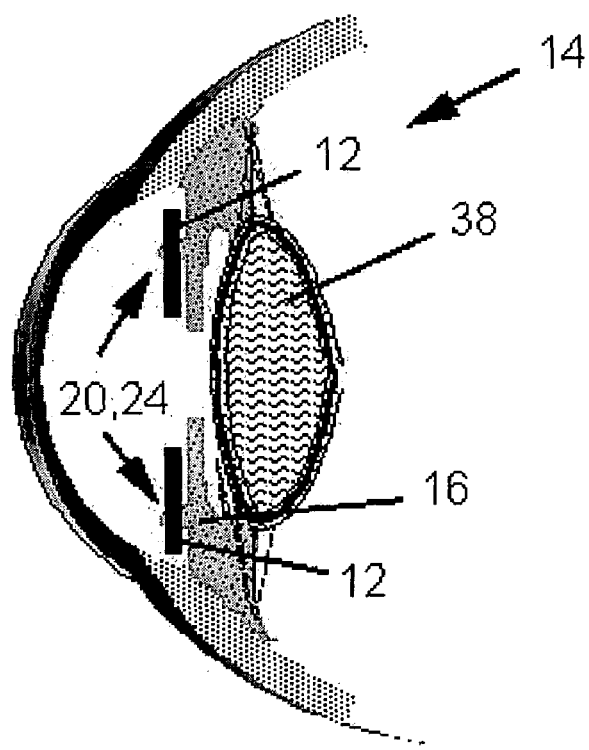
FIG. 4 is a sectional view of the implant according to FIGS. 1 to 3, wherein the implant rests on the iris and is attached thereto.

FIG. 4 shows a sectional view of the implant 10 according to FIGS. 1 to 3, wherein the implant 10 rests on the iris 16 and is attached thereto. One clearly recognizes that the implant 10 comes to rest with its annular area 12 on the iris 16. The partial areas of the iris 16 underlying the openings 24 are passed through the openings 24 and anchored therein. Further, one recognizes that the implant 10 allows for the unimpeded transmission of light through the pupil 38 into the eye 14 by its annular design. The method of locating and fixing said intraocular implant 10 for altering the iris color comprises the steps of: a) preparing the eye 14 to receive an intraocular implant 10; b) inserting the intraocular implant 10 into the eye 14 via a small cut in the eye 14; c) positioning said implant 10 on the iris 16 of the eye 14, wherein said annular area 12 comes to rest on the iris 16, said openings 24 serve for passing and anchoring the underlying partial areas of the iris 16 thereby attaching the implant 10 to the iris 16; and d) closing the eye 14 where said implant 10 was inserted. Said attachment step is carried out by passing said underlying partial areas of the iris 16 through the openings 24 with a spatula or another surgical instrument or by passing said underlying partial areas of the iris 16 through the openings 24 by suction with suction means.

Figure 5:
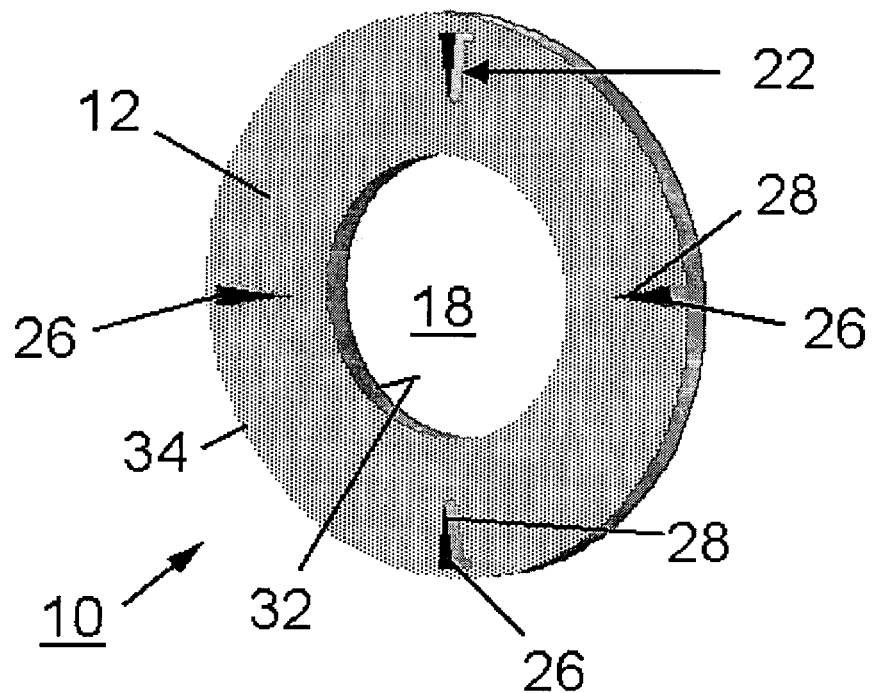
FIG. 5 is a schematic representation of an inventive implant according to a second embodiment.

FIG. 5 shows a schematic representation of an implant 10 according to a second embodiment. According to this second embodiment, the attaching means 22 each consist of a hook-like protrusion 26, wherein the protrusion 26 serves for penetrating and hooking the implant 10 into the corresponding partial areas of the iris 16. Therein, the protrusions 26 each have an exposed end 28, which is formed tapered and thus facilitates the penetration of the protrusions into the iris 16. Therein, the protrusions 26 consist of biocompatible material such as biocompatible plastics.

Also the implant 10 according to the illustrated second embodiment has circular edges 32, 34 and thus forms a ring. Therein, the central opening 18 of the ring serves for light transmission.

Figure 6:
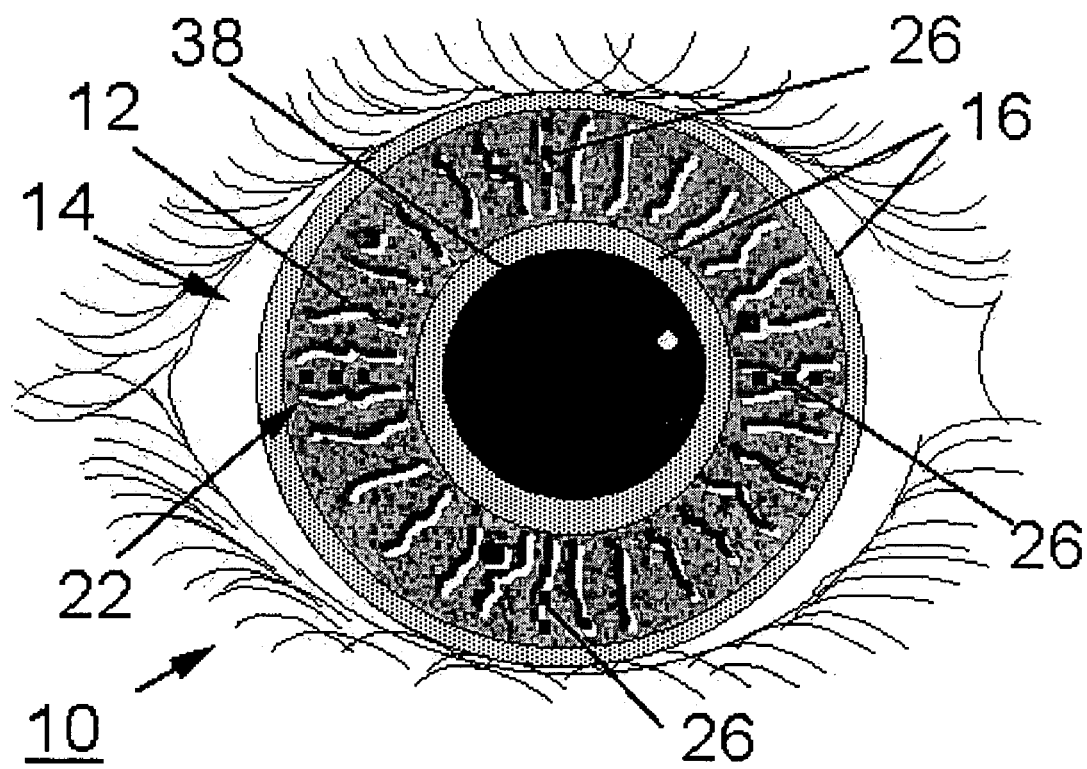
FIG. 6 is a representation of the implant according to FIG. 5, wherein the implant rests on an iris.

FIG. 6 shows a representation of the implant 10 according to FIG. 5, wherein the implant 10 rests on the iris 16. One recognizes also in this embodiment, that the attaching means 22, 26 are formed within the annular area 12 of the implant 10. Thus, the attaching means 22, 26 come to rest exclusively on the iris 16.

Figure 7:
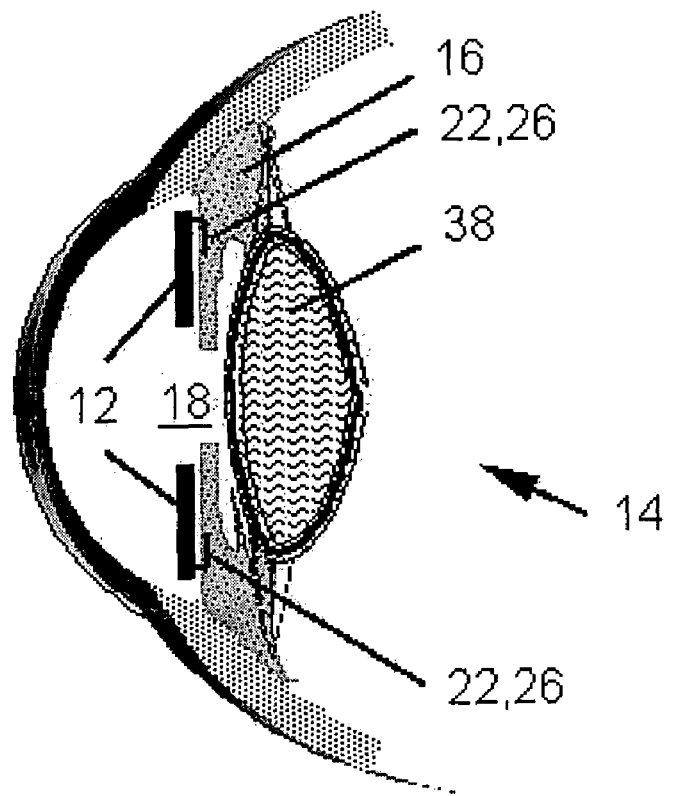
FIG. 7 is a sectional view of the implant according to FIGS. 5 and 6, wherein the implant rests on the iris and is attached thereto.

By the sectional view of the implant 10 according to the FIGS. 5 and 6, shown in FIG. 7, it is appreciable, how the implant 10 rests on the iris 16 and is attached thereto. One recognizes that the attaching means 22, 26 engage with the underlying partial areas of the iris 16. Therein, the hook-like protrusions 26 point toward the ring inner side of the implant 10. The central opening 18 surrounded by the annular area 12 allows for the unimpeded light transmission through the pupil 38 into the inside of the eye 14. The method of locating and fixing an intraocular implant for altering the iris color comprises the steps of: a) preparing the eye 14 to receive the intraocular implant 10; b) inserting the intraocular implant 10 into the eye 14 via a small cut in the eye 14; c) positioning said implant on the iris 16 of the eye 14, wherein said annular area 12 comes to rest on the iris 16, said hook-like protrusions 26 serve for penetrating and hooking the implant 10 into the corresponding partial areas of the iris 16 thereby attaching the implant 10 to the iris 16; and d) closing the eye 14 where the implant 10 was inserted.

Figure 8:
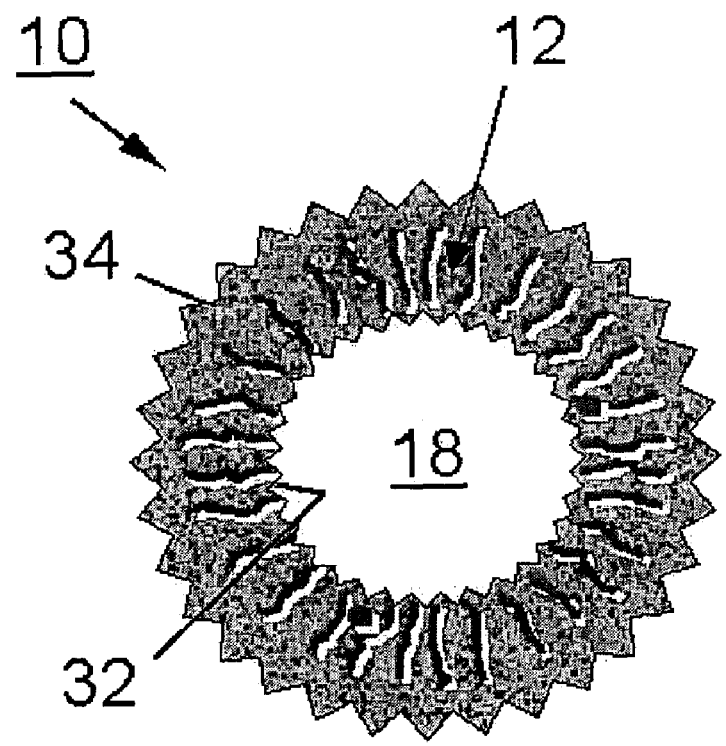
FIG. 8 is a schematic view of an inventive implant according to a third embodiment.

FIG. 8 shows a schematic view of an implant 10 according to a third embodiment. One recognizes that the edges 32, 34 of the implant are formed serrated. However, as a whole, the implant 10 is further formed annularly, i.e. the implant 10 again has an annular area 12 and a central opening 18. It is also possible that the edges 32, 34 of the implant 10 have another shape.

Figure 9:
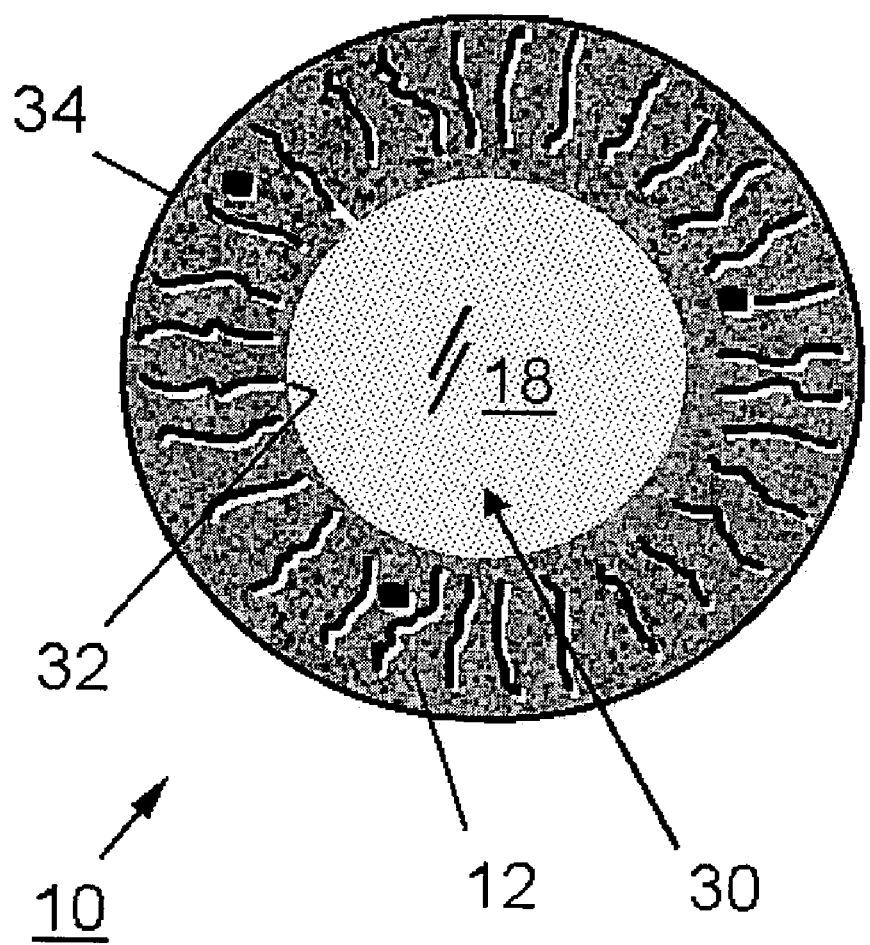
FIG. 9 is a schematic representation of an inventive implant according to a fourth embodiment.

FIG. 9 shows a schematic representation of the implant 10 according to a fourth embodiment. One recognizes that the annular implant 10 has an optical lens or a transparent foil 30 in the region of the central opening 18. Therewith it is possible, besides the alteration of the iris color or the iris pattern, respectively, to also perform a vision correction.

Although shown in only a few embodiments in the figures, it will be recognized from the description set out herein that the present invention contemplates implants which, although not constructed exactly as shown in the figures, function in substantially similar fashion to achieve substantially similar results as the implants which are shown. It has been noted, for instance, that the implant may have other shapes as described. All such changes are intended to fall within the spirit and scope of the following claims.

What is claimed is:

1. Implant for altering the iris color, comprising a completely or partially transparent, semi-transparent or non-transparent, colored, biocompatible and flexible material, wherein
the implant is formed annularly thereby forming an annular area coming to rest on the iris of an eye, and
said implant further comprising a central circular opening, and
at least one attaching means is formed for detachable attachment of the implant to the iris, wherein the attaching means is disposed within the annular area, and
wherein said attaching means comprises at least one opening in the annular area, the opening serving for passing and anchoring the underlying partial areas of the iris, and
wherein said opening is formed in the shape of cross-slits.

2. Implant according to claim 1, wherein said opening has at least one of (i) projections and (ii) a rough surface at its inner circumference.

3. Implant for altering the iris color, comprising a completely or partially transparent, semi-transparent or non-transparent, colored, biocompatible and flexible material, wherein
the implant is formed annularly thereby forming an annular area coming to rest on the iris of an eye, and
said implant further comprising a central circular opening, and
at least one attaching means is formed for detachable attachment of the implant to the iris, wherein the attaching means is disposed within the annular area, and
wherein said attaching means comprises at least one hook-like protrusion or projection, said protrusion or projection serving for penetrating and hooking the implant into the corresponding partial areas of the iris.

4. Implant according to claim 3, wherein said protrusion or projection comprises an exposed end that is formed tapered.

5. Implant according to claim 4, wherein said protrusion or projection comprises biocompatible material.

6. Implant according to claim 3, wherein said protrusion or projection comprises biocompatible material.

7. Implant according to claim 3, wherein one or both of said implant and said protrusion or projection comprises biocompatible plastic.

8. Implant for altering the iris color, comprising a completely or partially transparent, semi-transparent or non-transparent, colored, biocompatible and flexible material, wherein
the implant is formed annularly thereby forming an annular area coming to rest on the iris of an eye, and
said implant further comprising a central circular opening, and
at least one attaching means is formed for detachable attachment of the implant to the iris, wherein the attaching means is disposed within the annular area, and
wherein said implant has a diameter of 5 to 12 mm and a thickness of 50 to 300 μm.

9. Implant for altering the iris color, comprising a completely or partially transparent, semi-transparent or non-transparent, colored, biocompatible and flexible material, wherein
the implant is formed annularly thereby forming an annular area coming to rest on the iris of an eye, and
said implant further comprising a central circular opening, and
at least one attaching means is formed for detachable attachment of the implant to the iris, wherein the attaching means is disposed within the annular area, and wherein said central circular opening has a diameter adapted to the diameter of the implant of 5 to 7 mm.

10. Implant for altering the iris color, comprising a completely or partially transparent, semi-transparent or non-transparent, colored, biocompatible and flexible material, wherein
   the implant is formed annularly thereby forming an annular area coming to rest on the iris of an eye, and
   said implant further comprising a central circular opening, and
   at least one attaching means is formed for detachable attachment of the implant to the iris, wherein the attaching means is disposed within the annular area, and
   wherein said implant comprises edges and the edges are formed completely or partially irregularly or serrated.

11. A method of locating and fixing an intraocular implant for altering the iris color comprising the steps of:
   a) preparing an eye to receive an intraocular implant;
   b) inserting the intraocular implant into the eye via a small cut in the eye;
   c) positioning said implant on the iris of the eye, wherein said implant consists of a completely or partially transparent, semi-transparent or non-transparent, colored, biocompatible and flexible material and wherein said implant is formed annularly and forms an annular area coming to rest on the iris of said eye, said implant further comprising a central circular opening and at least one attaching means for a detachable attachment of the implant to the iris, wherein said attaching means is disposed within the annular area, wherein said attaching means comprises at least one opening in the annular area, wherein the opening serves for passing and anchoring the underlying partial areas of the iris thereby attaching said implant to the iris;
   d) attaching said implant to the iris; and
   e) closing the eye where said implant was inserted, and wherein said step of attaching comprises by passing said underlying partial areas of the iris through the opening by suction with a suction means.

12. A method of locating and fixing an intraocular implant for altering iris color comprising the steps of:
   a) preparing an eye to receive an intraocular implant;
   b) inserting the intraocular implant into the eye via a small cut in the eye;
   c) positioning said implant on the iris of the eye, wherein said implant consists of a completely or partially transparent, semi-transparent or non-transparent, colored, biocompatible and flexible material and wherein said implant is formed annularly and forms an annular area coming to rest on the iris of said eye, said implant further comprising a central circular opening and at least one attaching means for a detachable attachment of the implant to the iris, wherein said attaching means is disposed within the annular area, wherein said attaching means comprises at least one opening in the annular area, wherein the opening serves for passing and anchoring the underlying partial areas of the iris thereby attaching said implant to the iris;
   d) attaching said implant to the iris; and
   e) closing the eye where said implant was inserted, and wherein said opening is formed in the shape of cross-slits.

13. A method of locating and fixing an intraocular implant for altering the iris color comprising the steps of:
   a) preparing an eye to receive an intraocular implant;
   b) inserting the intraocular implant into the eye via a small cut in the eye;
   c) positioning said implant on the iris of the eye, wherein said implant consists of a completely or partially transparent, semi-transparent or non-transparent, colored, biocompatible and flexible material and wherein said implant is formed annularly and forms an annular area coming to rest on the iris of said eye, said implant further comprising a central circular opening and at least one attaching means for a detachable attachment of the implant to the iris, wherein said attaching means is disposed within the annular area, wherein said attaching means comprises at least one opening in the annular area, wherein the opening serves for passing and anchoring the underlying partial areas of the iris thereby attaching said implant to the iris;
   d) attaching said implant to the iris; and
   e) closing the eye where said implant was inserted, and wherein said opening has at least one of (i) projections and (ii) a rough surface at its inner circumference.

14. A method of locating and fixing an intraocular implant for altering the iris color comprising the steps of:
   a) preparing an eye to receive an intraocular implant;
   b) inserting the intraocular implant into the eye via a small cut in the eye;
   c) positioning said implant on the iris of the eye, wherein said implant consists of a completely or partially transparent, semi-transparent or non-transparent, colored, biocompatible and flexible material and wherein said implant is formed annularly and forms an annular area coming to rest on the iris of said eye, said implant further comprising a central circular opening and at least one attaching means for a detachable attachment of the implant to the iris, wherein said attaching means is disposed within the annular area wherein said attaching means comprises at least one opening in the annular area;
   d) attaching said implant to the iris; and
   e) closing the eye where said implant was inserted; and wherein the attaching means comprises at least one hook-like protrusion or projection, said protrusion or projection serving for penetrating and hooking said implant into the corresponding partial areas of the iris.

15. The method of claim 14, wherein said protrusion or projection comprises an exposed end that is formed tapered.

16. A method of implanting an intraocular implant for altering the iris color comprising:
   a) positioning the implant on the iris of the eye, wherein the implant consists of a completely or partially transparent, semi-transparent or non-transparent, colored, biocompatible and flexible material and wherein the implant is formed annularly and forms an annular area coming to rest on the iris of the eye, the implant further comprising a central circular opening and at least one attaching means for a detachable attachment of the implant to the iris, wherein the attaching means is disposed within the annular area, and wherein the attaching means comprises at least one hook-like protrusion or projection; and
   b) attaching the implant to the iris.

17. The method of claim 16, wherein the protrusion or projection comprises an exposed end that is tapered in shape.

* * * * *